United States Patent
Mandell

(10) Patent No.: US 9,186,545 B2
(45) Date of Patent: *Nov. 17, 2015

(54) EXERCISE DEVICE AND METHOD

(71) Applicant: Adult Fitness Concepts, LLC, Chevy Chase, MD (US)

(72) Inventor: David Mandell, Chevy Chase, MD (US)

(73) Assignee: Adult Fitness Concepts, LLC, Chevy Chase, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/317,866

(22) Filed: Jun. 27, 2014

(65) Prior Publication Data

US 2014/0309090 A1  Oct. 16, 2014

Related U.S. Application Data

(63) Continuation of application No. 13/468,840, filed on May 10, 2012, now Pat. No. 8,784,282.

(51) Int. Cl.

| | |
|---|---|
| *A63B 23/20* | (2006.01) |
| *A63B 71/00* | (2006.01) |
| *A61F 5/41* | (2006.01) |
| *A63B 21/06* | (2006.01) |
| *A63B 21/065* | (2006.01) |
| *A63B 21/00* | (2006.01) |

(52) U.S. Cl.
CPC . *A63B 23/20* (2013.01); *A61F 5/41* (2013.01); *A63B 21/06* (2013.01); *A63B 21/065* (2013.01); *A63B 21/1403* (2013.01); *A63B 21/1476* (2013.01); *A63B 71/0054* (2013.01); *A63B 2071/0072* (2013.01); *A63B 2071/0081* (2013.01); *A63B 2209/08* (2013.01)

(58) Field of Classification Search
CPC ...................................................... A63B 21/00
USPC ............................ 482/105, 93, 108, 110, 106
See application file for complete search history.

(56) References Cited

U.S. PATENT DOCUMENTS

| | | | | |
|---|---|---|---|---|
| 348,379 | A * | 8/1886 | Ceasar | 482/105 |
| 1,577,077 | A * | 3/1926 | Huston | 482/105 |
| 5,060,936 | A | 10/1991 | Ekonen et al. | |
| 5,702,330 | A | 12/1997 | De Monbrun et al. | |
| 7,211,031 | B1 * | 5/2007 | Soloviev | 482/105 |
| 7,448,989 | B2 * | 11/2008 | Dana, III | 482/105 |
| 2002/0153014 | A1 | 10/2002 | Cheng et al. | |
| 2003/0036464 | A1 | 2/2003 | Zavilevich | |
| 2005/0065000 | A1 | 3/2005 | Reinhart | |
| 2006/0116245 | A1 | 6/2006 | Palmenco-Geller et al. | |
| 2006/0270533 | A1 | 11/2006 | Dana, III | |
| 2012/0208680 | A1 | 8/2012 | Boyce | |

FOREIGN PATENT DOCUMENTS

| | | |
|---|---|---|
| CA | 2310002 | 9/2000 |
| WO | WO2010131252 | 11/2010 |

* cited by examiner

*Primary Examiner* — Jerome W Donnelly
(74) *Attorney, Agent, or Firm* — McHale & Slavin, P.A.

(57) ABSTRACT

An exercise device for the pubococcygeus muscle of a male person comprising a support member having two arms and a base, wherein the arms of support member are configurable to fit around the shaft of the penis of a male person so that the base depends from the penis.

7 Claims, 5 Drawing Sheets

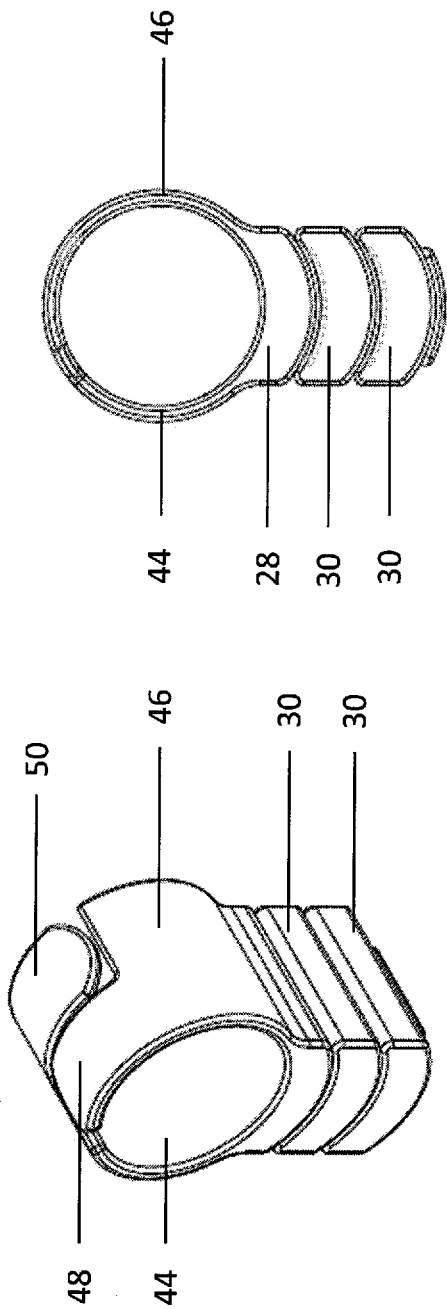

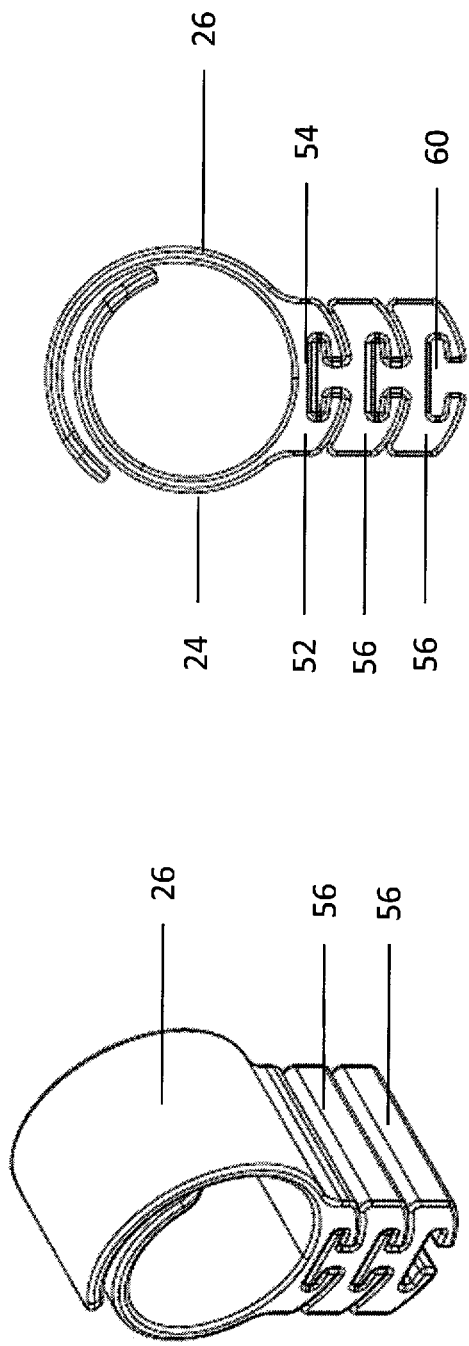
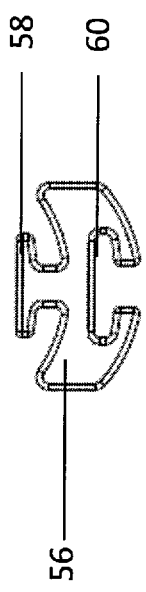
Fig. 10
Fig. 11
Fig. 9

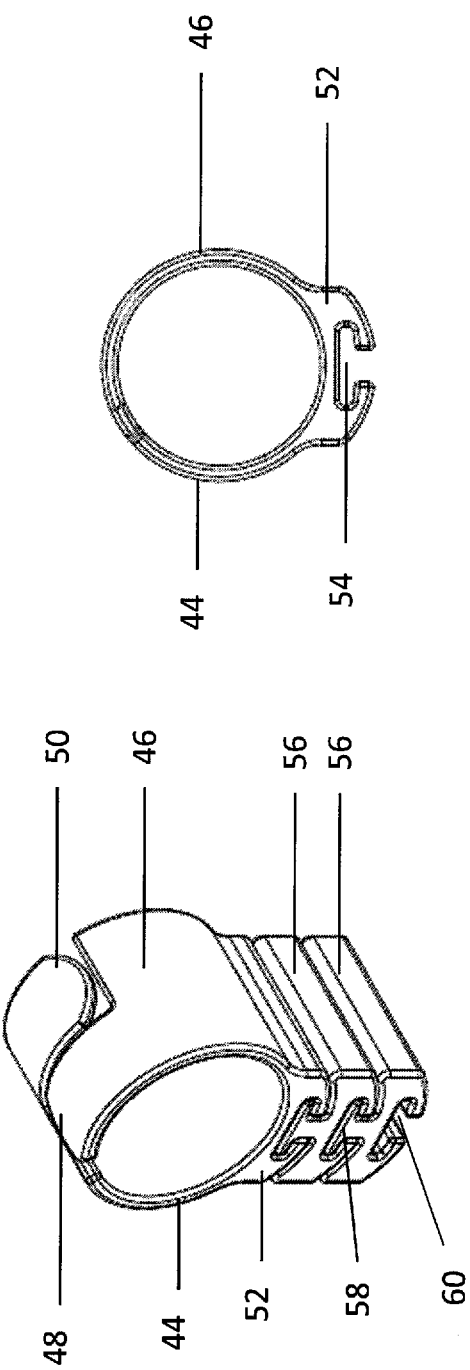

EXERCISE DEVICE AND METHOD

PRIORITY CLAIM

In accordance with 37 C.F.R. 1.76, a claim of priority is included in an Application Data Sheet filed concurrently herewith. Accordingly, the present invention claims priority as a continuation of U.S. patent application Ser. No. 13/468,840, entitled "EXERCISE DEVICE AND METHOD", filed May 10, 2012. The contents of the above referenced application is incorporated herein by reference.

FIELD OF THE INVENTION

The present invention relates to exercise devices for enhanced sexual function and for the prevention of incontinence, and more particularly, to a device and method for performing male Kegel exercises.

BACKGROUND OF THE INVENTION

The muscles surrounding the base of the penis, anus and prostate gland are known as the pubococcygeus muscles. Exercises of the pubococcygeus muscles were developed by Dr. Arnold Kegel in the mid-1940's to prepare women for the physiological stresses of the late stages of pregnancy and vaginal childbirth. It was later discovered that the exercises, when performed by men, provided significant benefits.

Typically, Kegel exercises are performed by an individual in private without a device that provides resistance. For men, exercising the pubococcygeus muscles can create harder and firmer erections, improve sexual performance, heighten orgasms, aid in reducing premature ejaculation, and improve prostate health. Additionally, there is evidence that exercising the pubococcygeus muscles may help prevent and treat urinary incontinence.

For men, Kegel exercises typically consist of a series of motions in which the individual squeezes and releases his pubococcygeus muscles. Dr. Kegel, in his research, however, also noted that adding resistance to these exercises further developed and strengthened the pubococcygeus muscles and could lead to more significant results.

Prior attempts at devices for providing resistance for Kegel exercises suffer from at least one of the following shortcomings: the devices are cumbersome and difficult to use, the devices pose a risk of injury to a user, the devices are intimidating, unattractive, and not designed for the mainstream consumer, the devices do not allow the user to provide assistance to himself during the workout, the devices are ineffective, or the devices are hard to clean and maintain.

Accordingly, there is a need for an improved device and method for performing male Kegel exercises that remedy the shortcomings of the prior art.

SUMMARY OF INVENTION

Accordingly, the present invention is directed to an improved device and method for performing male Kegel exercises that provides resistance with an easy-to-use device that is positioned on the shaft of the penis. The device offers a series of magnetic or clip on weights that hang straight down and can be easily added or removed during exercise to adjust weight levels. The design also enables the user to provide assistance to himself during the workout (also known as "spotting") which enables the user to create greater pubococcygeus muscle fatigue and improves the effectiveness of the workout. In addition, the design can be easily cleaned and maintained.

The present invention according an embodiment is directed to an exercise device for the pubococcygeus muscle of a male person, the device comprising: a support member having two arms and a base. The arms of support member are configurable to fit around the shaft of the penis of a male person so that the base depends from the penis. The base may further comprise an enclosed weight.

In one embodiment, one of the arms is configured to partially and adjustably nest within the other arm to form a complete ring. In an additional embodiment, one of the arms has a plurality of holes and the other arm has a pin configured for lockable engagement in one of the holes. In another embodiment, the arms have interlocking portions, the arms being configured so that the interlocking portions are movable relative to each other but still form a closed ring.

The exercise device may further have at least one supplemental weight coupleable to the base. In one embodiment, the base has a magnet and the supplemental weight further comprises a magnet; and the supplemental weight is magnetically coupleable to the base. The base may further comprise a tab, and the supplemental weight may further comprise an indentation; the tab being configured to rest within the indentation when the base and supplemental weight are properly oriented for coupling.

In an additional embodiment, the base has a slot on a bottom side, the supplemental weight has a key on a top side; and the supplemental weight key is configured for engagement with the base slot for coupling the supplemental weight to the base. The supplemental weight may have a slot on a bottom side for coupling the supplemental weight to an additional supplemental weight.

The present invention, according to another embodiment, is directed to an exercise device for the pubococcygeus muscle of a male person, the device comprising: two arms; a base coupled to the two arms, the base further comprising an enclosed weight; and at least one supplemental weight coupleable to the base. The arms are configured to form an adjustable ring around the shaft of the penis of a male person so that the base depends from the penis.

Optionally, one of the arms is configured to partially and adjustably nest within the other arm to form a complete ring. In an additional embodiment, one of the arms has a plurality of holes and the other arm has a pin configured for lockable engagement in one of the holes. In an alternative embodiment, the arms have interlocking portions and the arms are configured so that the interlocking portions are movable relative to each other but still form a closed ring.

Optionally, the base has a magnet, the supplemental weight has a magnet and the supplemental weight is magnetically coupled to the base. Optionally, the base has a slot on a bottom side, the supplemental weight further has a key on a top side; and the supplemental weight key is configured for engagement with the base slot to couple the supplemental weight to the base.

The present invention is also directed to a method for exercising the pubococcygeus muscle of a male person, the method comprising the steps of: (a) providing an exercise device having two arms and a base; (b) placing the arms of the exercise device around an erect penis of the male person, such that the device is retained on the penis with the base depending from the penis; and (c) performing Kegel exercises with the exercise device placed in accordance with step (b). Preferably, the exercise device is retained on the shaft of the penis near the head of the penis. Additionally, the method may further comprise: selecting at least one supplemental weight, and coupling the at least one supplemental weight to the base. Additionally, the method may further comprise coupling at least one supplemental weight to another supplemental weight that has already been coupled to the base.

BRIEF DESCRIPTION OF THE DRAWINGS

The features, aspects and advantages of the present invention will become better understood with regard to the following description, appended claims and accompanying figures wherein:

FIG. 7 is a perspective elevation view of an exercise device according to a third embodiment of the present invention;

FIG. 8 is an elevation view of the exercise device of FIG. 7;

FIG. 9 is a perspective elevation view of an exercise device according to a fourth embodiment of the present invention;

FIG. 10 is an elevation view of the exercise device of FIG. 9;

FIG. 11 is an elevation view of a weight usable in the exercise device of FIG. 9;

FIG. 12 is a perspective elevation view of an exercise device according to a fifth embodiment of the present invention; and FIG. 13 is an elevation view of the exercise device of FIG. 12 without supplemental weights.

DETAILED DESCRIPTION OF THE PREFERRED EMBODIMENTS

Figure 2:
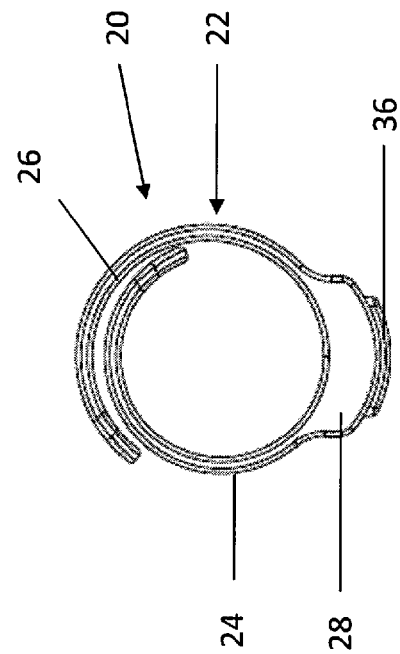
FIG. 2 is an elevation view of the exercise device of FIG. 1 without supplemental weights.

In the following description of the preferred embodiments, reference is made to the accompanying drawings which show by way of illustration specific embodiments in which the invention may be practiced. Wherever possible, the same reference numbers will be used throughout the drawings to refer to the same or like parts. It is to be understood that other embodiments may be utilized and structural, and functional changes may be made without departing from the scope of the present invention.

An exercise device according to a first embodiment of the present invention is shown in FIGS. 1 to 4. The exercise device 20 has a support member 22. The support member 22 has two arms 24, 26 and a base 28. The arms 24, 26 extend from the base 28 and are precurved to form an adjustable ring configured to fit around the shaft of a male person's penis. In the first embodiment, one of the arms is configured to partially and adjustably nest within the other arm to form a complete ring around the penis. In an alternative embodiment, the support member 22 may be formed of a single curved arm.

Preferably the arms 24, 26 are made of molded rubber or plastic, and more preferably of rubber or plastic over a resilient metal, such that the arms can be moved relative to one another to allow the device to fit around differently sized penises, yet are rigid enough that the arms cannot be bent under weight to completely disengage from the shaft of the user's penis. In a preferred embodiment, the arms 24, 26 are made of a thermoplastic elastomer formed over spring steel.

The base 28 is coupled to the arms 24, 26. Preferably, the base 28 is made of rubber or plastic and is molded at the same time as the arms. However, the base 28 may be made of different material than the arms and may be coupled to the arms. In an embodiment, a base weight is molded into the base 28. The base weight may be made from any reasonably dense material. In an embodiment, the base weight is made from metal, such as steel, iron or lead. The base weight can be molded into the base or coupled to the base. The base weight may weigh from about 6 ounces to about 24 ounces, and more preferably from about 2 ounces to about 3 ounces.

In an embodiment, the exercise device 20 further comprises at least one supplemental weight 30 coupleable to the base 28. The supplemental weight 30 may include a weight source 32 made from the same material as the base weight. Alternatively, the supplemental weights 30 can be made from a different material than the base weight. Preferably, the weight source is molded into a plastic or rubber casing 34 that matches the material of the support member 22.

Figure 4:
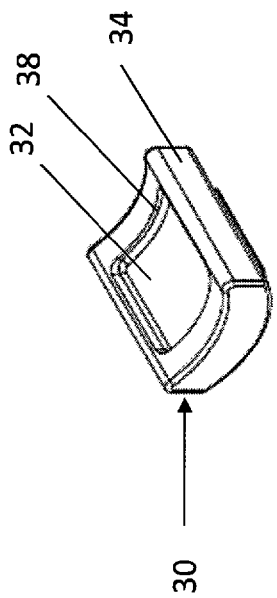
FIG. 4 is a perspective elevation view of a weight usable in the exercise device of FIG. 1.
Figure 1:
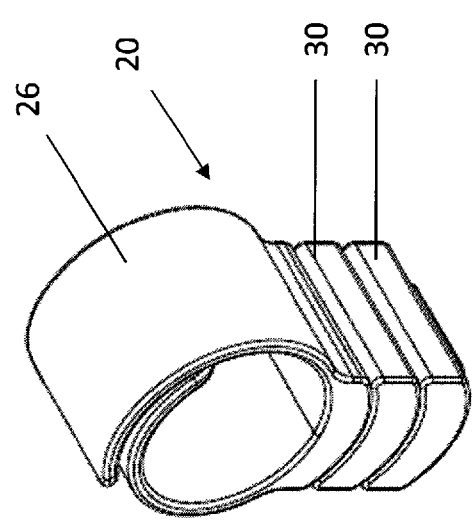
FIG. 1 is a perspective elevation view of an exercise device according to a first embodiment of the present invention.
Figure 3:
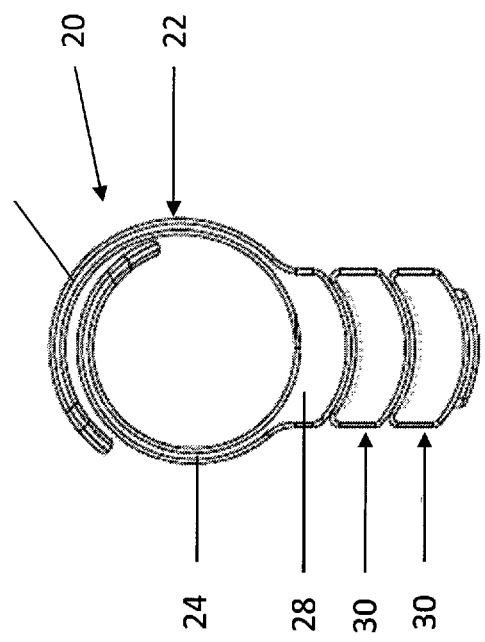
FIG. 3 is an elevation view of the exercise device of FIG. 1 with supplemental weights.

Preferably, as shown in FIGS. 1, 2 and 4, the exercise device 20 has a plurality of supplemental weights 30 that are attachable to each other and to the base 28. In an embodiment, the supplemental weights 30 each have the same weight. In an alternative embodiment, the supplemental weights 30 have different weights. Each supplemental weight may weigh from about 2 ounces to about 6 ounces, and more preferably from about 2 ounces to about 4 ounces.

In the embodiment shown in FIGS. 1 to 4 the base weight and supplemental weights 30 are magnets. The supplemental weights 30 may be magnetically coupled to each other and to the base 28. Preferably, the base 28 has a tab 36 on a bottom side and the supplemental weight 30 has an indentation 38 on a top side, each such that the base tab 36 may engage with the indentation 38 to fit the supplemental weight 30 on the base. The engagement of the tab 36 and the indentation 38 preferably allows for optimum positioning of the magnetic base weight and magnetic supplemental weight. Preferably, each supplemental weight 30 has a tab 36 on a bottom side for engagement with the indentation 38 of another supplemental weight 30 to allow multiple supplemental weights to be fitted to the base 28. As will be understood by one of skill in the art, the configuration of the tab and the indentation may be reversed such that the base has an indentation, and the supplemental weight has a tab on a top side and an indentation on a bottom side.

Figure 6:
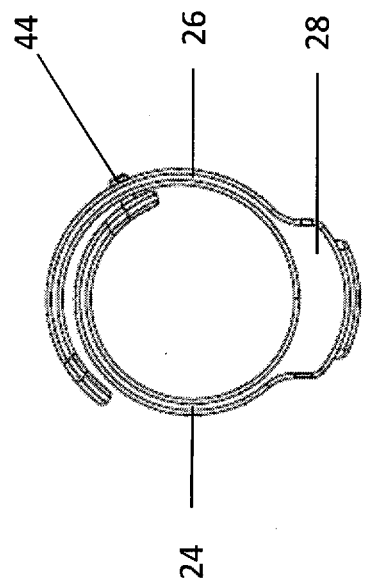
FIG. 6 is an elevation view of the exercise device of FIG. 5 without supplemental weights.
Figure 5:
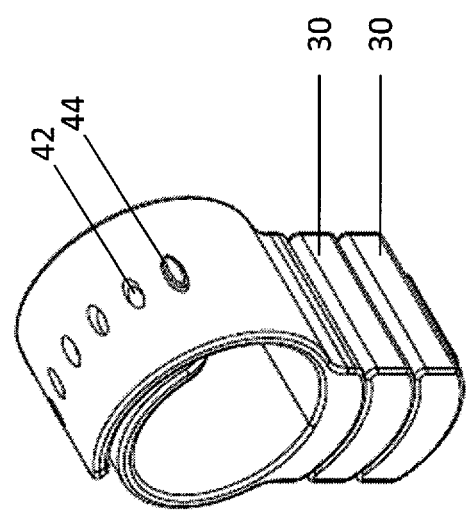
FIG. 5 is a perspective elevation view of an exercise device according to a second embodiment of the present invention.

A second embodiment of the present invention is shown in FIGS. 5 and 6. In the second embodiment, one of the arms has a plurality of holes 42 along its length and the other arm has a pin 44 configured for lockable engagement in one of the holes 42. The holes 42 and the pin 44 allows for a user to set the size of the ring formed by the arms. This may allow for a more comfortable fit, and may also allow for the use of less resilient materials for the arms. The number of holes and pins may be varied.

A third embodiment of the present invention is shown in FIGS. 7 and 8. In the third embodiment, as in the first embodiment, the exercise device 20 has a support member 22 and a base 28. The support member 22 has two arms 44, 46 that extend from the base 28 and are precurved to form an adjustable ring configured to fit around the shaft of a male person's penis. The arms 44, 46 are pliable and have interlocking portions 48, 50 that can be moved relative to one another to accommodate differently sized penises, yet together still form a closed ring to prevent the device from completely disengaging from the shaft of the user's penis during exercises when weights are used.

A fourth embodiment of the present invention is shown in FIGS. 9 to 11. The fourth embodiment contains arms as previously described with regard to the first embodiment shown in FIGS. 1 to 4. However, the support member 22 has a differently configured base 52. The base has a t-shaped slot 54 extending longitudinally along a bottom side. The supplemental weight 56 has a t-shaped key 58 extending longitudinally along a top side configured such that the supplemental weight key 58 may engage with the base slot 54 to securely couple the supplemental weight 56 to the base 52. Preferably, as shown in FIG. 11, each supplemental weight has a t-shaped slot 60 on a bottom side for engagement with the key 58 of another supplemental weight 56 to allow multiple supplemental weights to be fitted to the base 52.

The use of a key and slot mechanism for attaching the supplemental weights 56 to the base 52 allows for the use of non-magnetized bases and supplemental weights. Preferably, the outer covering of the base 52 and the supplemental weights has a high enough coefficient of static friction to prevent movement of the supplemental weights 56 relative to the base 52 during normal exercise usage.

As will be understood by one of skill in the art, the configuration of the key and the slot may be reversed such that the base has a key extending longitudinally along a bottom side, the supplemental weight has a key shaped slot extending longitudinally along a top side. Additionally, the supplemental weight may have a key extending longitudinally along a bottom side for engagement with the slot of another supplemental weight to allow multiple supplemental weights to be fitted to the base.

A fifth embodiment of the present invention is shown in FIGS. 12 and 13. The fifth embodiment contains arms 44, 46 with overlapping portions 48, 50 as previously described with regard to the third embodiment shown in FIGS. 7 and 8. The fifth embodiment further contains a base 52 having a t-shaped slot 54 and supplemental weights 56 having a t-shaped key 58 and a t-shaped slot 60 as described with regard to the fourth embodiment shown in FIGS. 9 to 11.

A method of using an exercise device in accordance with the present invention will now be described. A user is provided with an exercise device comprising a support member with two arms and a base. The arms of the support member are manipulated to securely place the exercise device on an erect penis of the male person with the base depending from the penis. The user then performs Kegel exercises with the exercise device placed on the penis. Preferably, the exerciser is placed such that the support member is retained on the shaft of the penis proximal to the head of the penis.

In an additional embodiment, the user selects at least one supplemental weight and attaches the supplemental weight to the base of the exercise device. The at least one supplemental weight may be selected from a plurality of different supplemental weights. A plurality of supplemental weights may be attached with a first supplemental weight being attached to the base and additional supplemental weights attached to the last already attached supplemental weight.

There is disclosed in the above description and the drawings, an exercise device which overcomes the disadvantages associated with the prior art. However, it will be apparent that variations and modifications of the disclosed embodiments may be made without departing from the principles of the invention. The presentation of the preferred embodiments herein is offered by way of example only and not limitation, with a true scope and spirit of the invention being indicated by the following claims.

Any element in a claim that does not explicitly state "means" for performing a specified function or "step" for performing a specified function, should not be interpreted as a "means" or "step" clause as specified in 35 U.S.C. §112.

What is claimed is:

1. An exercise device for the pubococcygeus muscle of a male person, the device comprising:
    a support member having two arms, said arms are configurable to fit around the shaft of the penis of a male person;
    a base secured to said arms so that said base depends from said penis, said base constructed and arranged to cooperate with at least one supplemental weight; and
    said at least one supplemental weight magnetically coupleable to said base.

2. The exercise device of claim 1, wherein one of said arms is configured to partially and adjustably nest within the other said arm to form a complete ring, said arms configured to disengage upon application of a predetermined weight.

3. The exercise device of claim 1, wherein said arms are constructed of a spring steel to encircle the shaft of the penis, and configured to disengage upon application of a predetermined weight.

4. The exercise device of claim 1, wherein one said arm has a tab and other said arm as an indentation, wherein said tab is configured to rest within said indentation when said arms are properly oriented for coupling, and configured to disengage upon application of a predetermined weight.

5. The exercise device of claim 1, wherein said arms are weighted.

6. The exercise device of claim 1, wherein said base and each said supplemental weight includes a magnet, wherein said supplemental weight is magnetically coupleable to said base and magnetically coupleable to each other.

7. The exercise device of claim 6, wherein a magnetic force exists between said supplemental weight and said base and between said supplemental weights, wherein said supplemental weight disengages from said base when said magnetic force is exceeded by a predetermined weight provided by said supplemental weights.

* * * * *